United States Patent
Aihara et al.

(10) Patent No.: US 10,489,666 B2
(45) Date of Patent: Nov. 26, 2019

(54) IMAGING DEVICE AND IMAGING SYSTEM

(71) Applicant: Panasonic Intellectual Property Management Co., Ltd., Osaka (JP)

(72) Inventors: Masayuki Aihara, Osaka (JP); Hisayoshi Yamamoto, Osaka (JP); Shigenori Yatsuri, Osaka (JP); Yoshio Matsumura, Osaka (JP); Hiroyuki Shobayashi, Hyogo (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 16/190,520

(22) Filed: Nov. 14, 2018

(65) Prior Publication Data
US 2019/0188504 A1    Jun. 20, 2019

(30) Foreign Application Priority Data

Dec. 18, 2017 (JP) ................................. 2017-242034
Sep. 13, 2018 (JP) ................................. 2018-171031

(51) Int. Cl.
*H04N 5/33* (2006.01)
*G06K 9/00* (2006.01)
*H04N 5/232* (2006.01)
*H04N 5/225* (2006.01)

(52) U.S. Cl.
CPC ..... *G06K 9/00838* (2013.01); *G06K 9/00604* (2013.01); *H04N 5/2253* (2013.01); *H04N 5/23219* (2013.01); *H04N 5/23232* (2013.01); *H04N 5/332* (2013.01)

(58) Field of Classification Search
CPC . G06K 9/00838; G06K 9/00604; H04N 5/332
See application file for complete search history.

(56) References Cited

U.S. PATENT DOCUMENTS

| 2012/0087541 A1* | 4/2012 | Hiroshi | G06K 9/00845 |
| | | | 382/103 |
| 2017/0217369 A1 | 8/2017 | Endo et al. | |

FOREIGN PATENT DOCUMENTS

| DE | 102013221882 | * | 4/2015 | ......... G01B 13/0005 |
| DE | 102013221882 A1 | | 4/2015 | |
| JP | 2003-104132 | | 4/2003 | |

(Continued)

OTHER PUBLICATIONS

The Extended European Search Report dated Apr. 18, 2019 for the related European Patent Application No. 18207388.2.

(Continued)

*Primary Examiner* — Tsion B Owens
(74) *Attorney, Agent, or Firm* — Renner, Otto, Boisselle & Sklar, LLP

(57) ABSTRACT

An object of the present disclosure is to increase resolution of a part required for sensing while achieving a wide view angle. An imaging device according to the present disclosure includes an image sensor and an optical system. An imaging surface of the image sensor includes a first region and a second region different from the first region. The optical system forms a subject image on the imaging surface so as to cause resolution of an image in the first region to be higher than resolution of an image in the second region. The first region is arranged so as to include a region where an image of a person's face is formed on the imaging surface.

10 Claims, 18 Drawing Sheets

(56) References Cited

FOREIGN PATENT DOCUMENTS

| JP | 2008-005137 | | 1/2008 | |
|---|---|---|---|---|
| JP | 2009-278185 | | 11/2009 | |
| JP | 2009278185 | * | 11/2009 | ............ H04N 5/232 |
| JP | 2014-210477 | | 11/2014 | |
| JP | 2015-226233 | | 12/2015 | |

OTHER PUBLICATIONS

Simon Thibault et al: "Enhanced optical design by distortion control", Proceedings of SPIE, vol. 5962, Sep. 30, 2005 (Sep. 30, 2005), pp. 596211-596211-8, XP055166771.

* cited by examiner

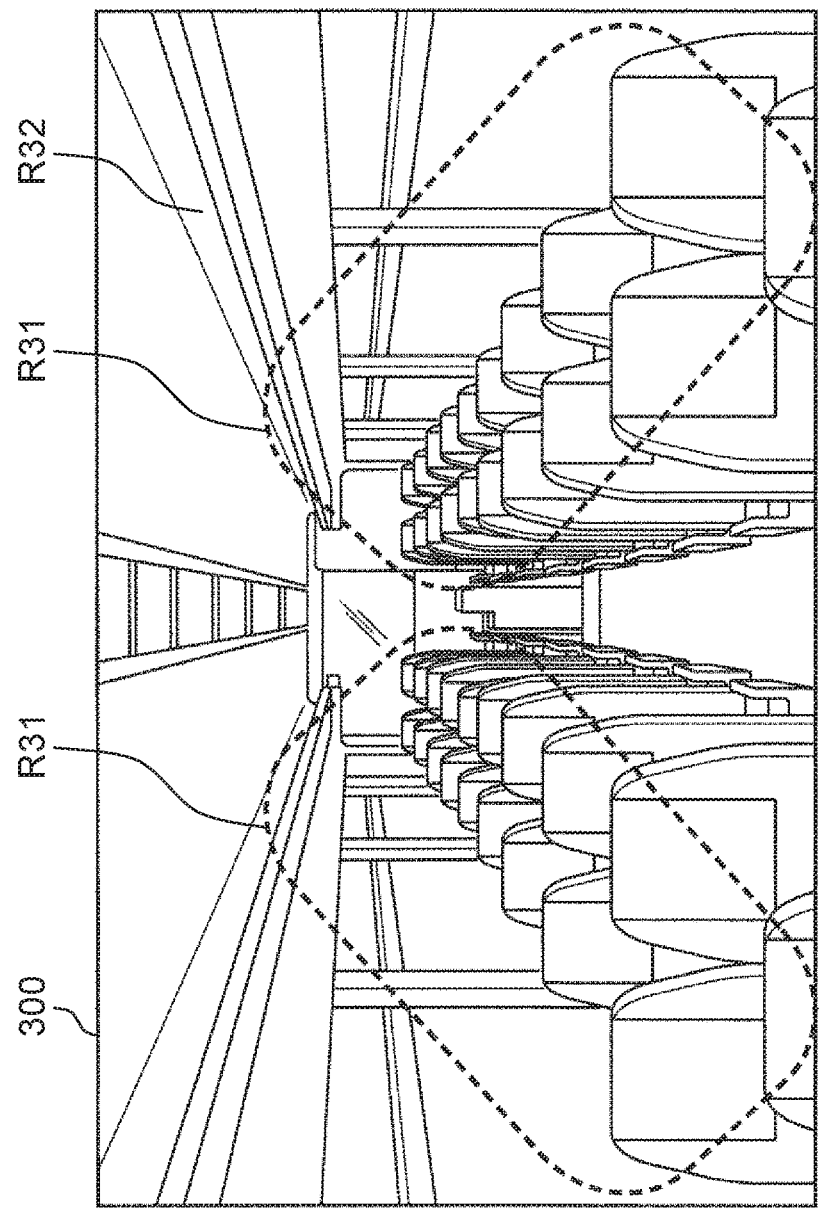

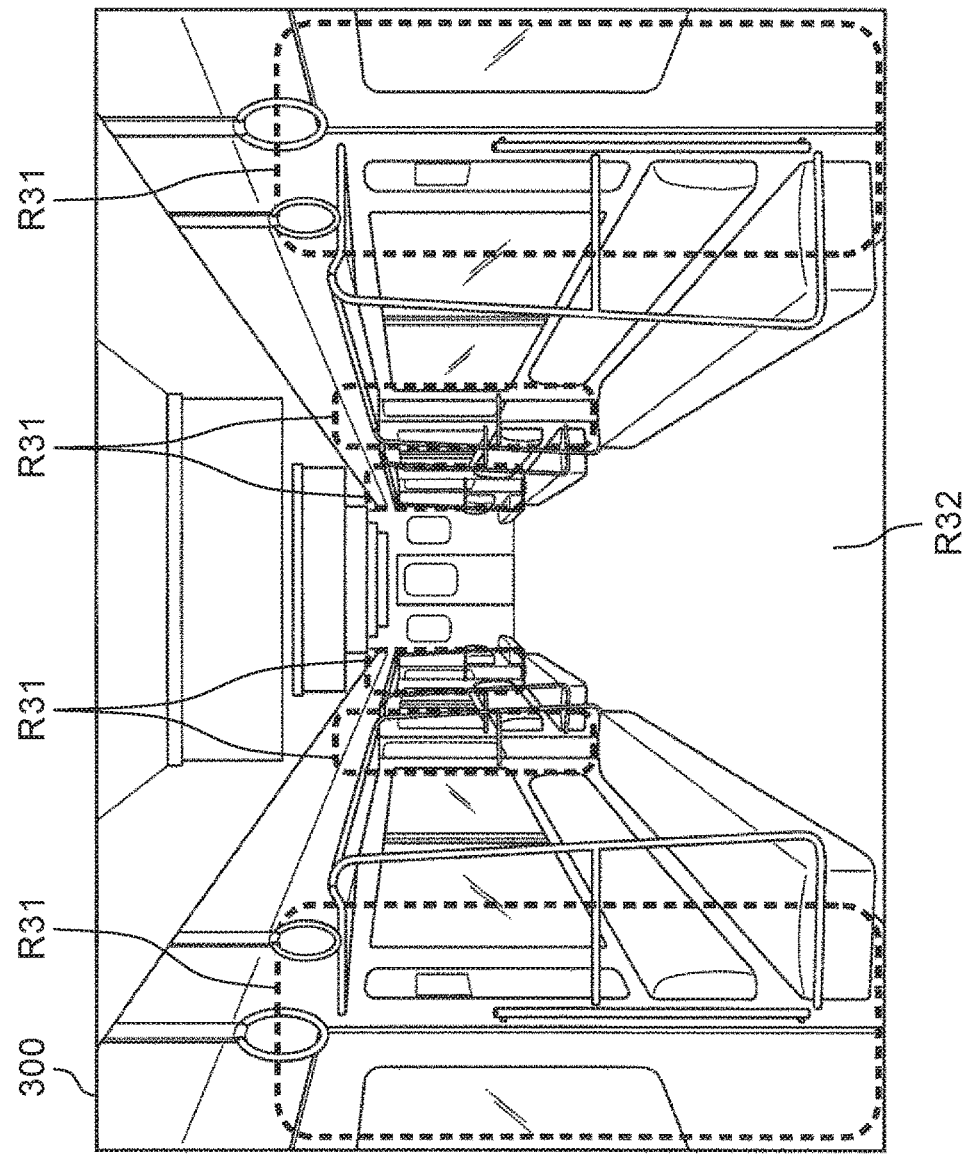

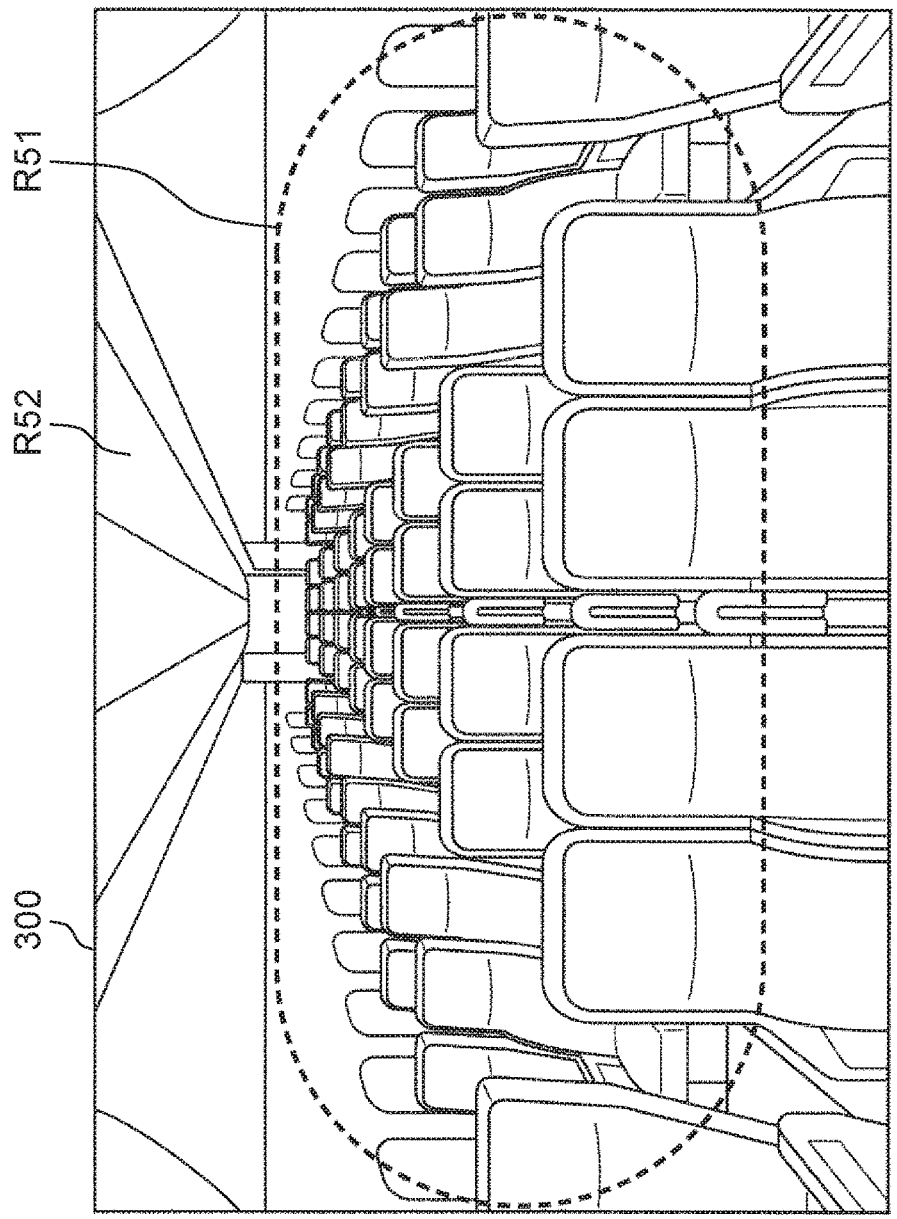

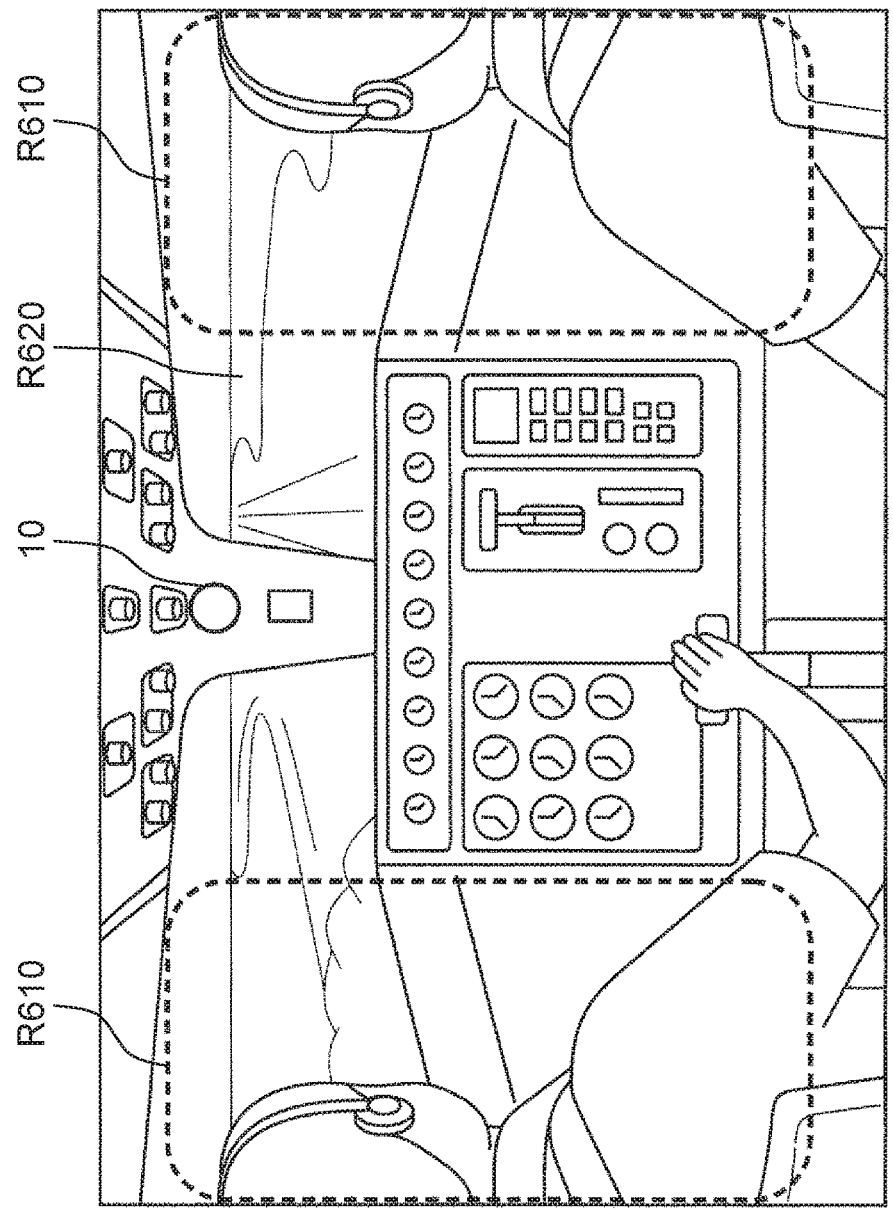

IMAGING DEVICE AND IMAGING SYSTEM

BACKGROUND

1. Technical Field

The present disclosure relates to an imaging device that captures an image and an imaging system.

2. Description of the Related Art

Unexamined Japanese Patent Publication No. 2014-210477 discloses an occupant detector that includes an image acquisition unit, a vehicle information acquisition unit, and an occupant detecting unit. The image acquisition unit acquires a captured image of a compartment of a vehicle from a camera that captures an image of the compartment. The vehicle information acquisition unit acquires vehicle information about the movement of a vehicle, which is detected in the vehicle. The occupant detecting unit determines whether an object present in a compartment is an occupant based on an image variation over time in an image region where an image of the object is formed, the image variation being detected based on a captured image, and vehicle information at a timing when the movement of the object is detected, and detects an occupant.

With this configuration, it is detected that the object in the compartment is an occupant based on the relationship between the movement of a vehicle and the movement of the object in the compartment. It is thus possible to distinguish the passenger from baggage or a virtual image formed by ambient light, thus achieving detection of the passenger in the compartment with high precision.

SUMMARY

When an image of a compartment is captured, it is desirable to capture the image at a wide angle for the purpose of obtaining information as much as possible. If a view angle is increased, however, the number of pixels per unit area in the image is reduced and the quality of an image of a subject (for example, an occupant's face) is degraded accordingly. Consequently, in analyzing an image captured at a wide angle, the number of pixels required for analysis becomes insufficient and thus the precision of the analysis is degraded.

The present disclosure provides an imaging device that can obtain an image of a region corresponding to an important part for image analysis (for example, a person's face) with high resolution, while achieving a wide view angle.

An imaging device according to the present disclosure includes an image sensor that has an imaging surface on which a plurality of pixels are two-dimensionally arranged and that generates image data from a subject image formed on the imaging surface and an optical system that forms the subject image in a predetermined range of a vertical view angle and in a predetermined range of a horizontal view angle on the imaging surface.

A number of pixels used for capturing the subject image included in a unit view angle is defined as resolution. The imaging surface includes a first region and a second region different from the first region.

The optical system forms the subject image on the imaging surface so as to cause resolution of a first subject image of the subject image in the first region to be higher than resolution of a second subject image of the subject image in the second region. The first region is arranged so as to include a region where an image of a person's face is formed on the imaging surface.

An imaging system according to the present disclosure includes the imaging device and a control device that analyzes the image data generated by the imaging device. The control device analyzes an image formed in the first region in an image indicated by the image data.

The present disclosure can provide an imaging device that can obtain an image of a region corresponding to an important part for image analysis (for example, a person's face) with high resolution, while achieving a wide view angle.

BRIEF DESCRIPTION OF THE DRAWINGS

FIG. 15 is an explanatory diagram of a magnified region when the imaging device according to the first exemplary embodiment is used for a bus;

FIG. 16 is an explanatory diagram of a magnified region when the imaging device according to the first exemplary embodiment is used for a railway vehicle;

FIG. 17 is an explanatory diagram of a magnified region when the imaging device according to the first exemplary embodiment is used for an airplane; and FIG. 18 is an explanatory diagram of a magnified region when the imaging device according to the first exemplary embodiment is used for a cockpit of the airplane.

DETAILED DESCRIPTION

Exemplary embodiments will be described in detail below with reference to the drawings as appropriate. However, descriptions in more detail than necessary may be omitted.

For example, detailed descriptions of well-known matters and duplicate descriptions of substantially identical configurations may be omitted. This is to avoid unnecessarily redundancy in the following description, and to facilitate understanding by those skilled in the art.

Here, the inventors of the present disclosure provide the accompanying drawings and the following description such that those skilled in the art can fully understand the present disclosure, and therefore, they do not intend to restrict the subject matters of claims by the accompanying drawings and the following description.

(First Exemplary Embodiment)

[1-1. Overall Configuration]

Figure 1:
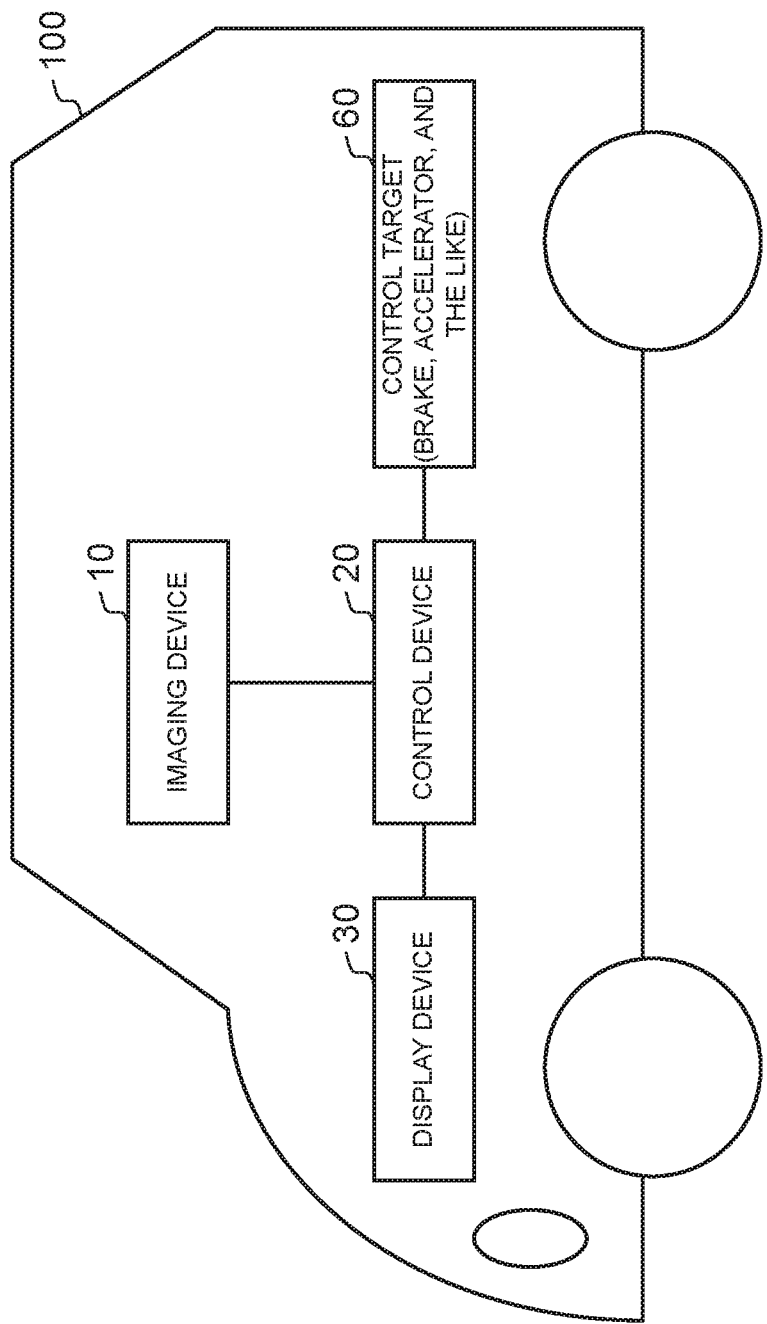
FIG. 1 shows a configuration of an imaging system, which is mounted on an automotive vehicle, according to an exemplary embodiment of the present disclosure.

FIG. 1 shows an example of using an imaging device according to the present disclosure as a camera in a compartment of an automobile as an example of a movable body. In the example of FIG. 1, imaging device 10 is mounted on vehicle 100 of an automobile so as to capture an image of occupants in the vehicle.

Vehicle 100 includes imaging device 10, control device 20, display 30, and control target 60. Imaging device 10 captures an image of a subject to generate image data. Control device 20 processes the image data from imaging device 10. Display 30 displays an image based on the image data processed by control device 20. Control target 60 is controlled by control device 20. Imaging device 10 and control device 20 constitute an imaging system.

Display 30 includes a display device such as a liquid crystal display panel or an organic electro luminescence (EL) display and a drive circuit for driving the display device. Display 30 is an electronic room mirror, an in-vehicle display, or the like and is capable of displaying various information (maps, route guides, radio station selections, various settings, and the like). Display 30 is also capable of displaying an image of inside of the vehicle captured by imaging device 10.

Control device 20 receives image data from imaging device 10, performs image analysis on the image data to detect a predetermined condition, and controls control target 60 based on a detection result. For example, control target 60 is at least one of a brake, an accelerator, a steering, and an alarm. Control device 20 also performs predetermined image processing on the image data from imaging device 10 to generate image data to be displayed on display 30.

Configurations of imaging device 10 and control device 20 will be specifically described below.

[1-1-1. Control Device]

Figure 2:
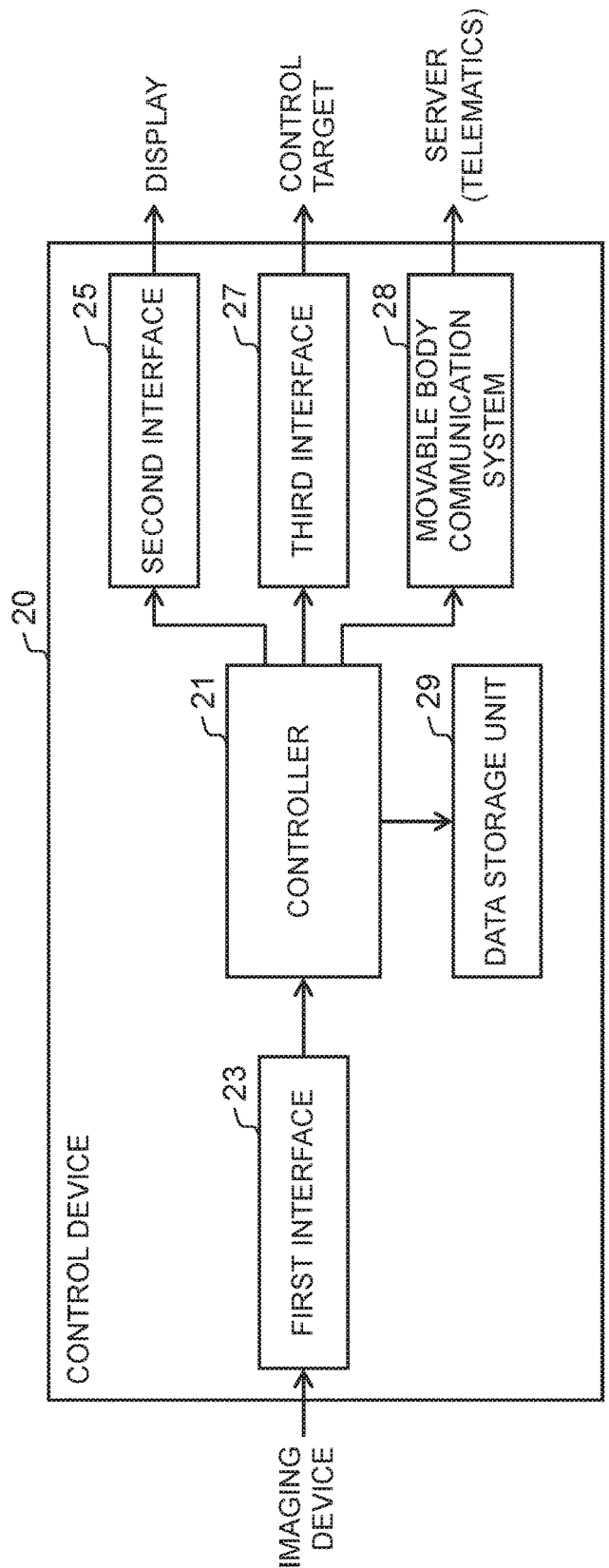
FIG. 2 shows a configuration of a control device in the imaging system.

FIG. 2 is a block diagram of a configuration of control device 20. Control device 20 includes first interface 23, controller 21, and data storage unit 29. First interface 23 inputs image data from imaging device 10. Controller 21 performs image processing and image analysis on the input image data. Data storage unit 29 stores data and the like. Control device 20 also includes second interface 25, third interface 27, and movable body communication system 28. Second interface 25 transmits the image data generated by controller 21 to display 30. Third interface 27 transmits a control signal for controlling control target 60 to control target 60. Movable body communication system 28 transmits and receives telematics information to and from a cloud server.

Controller 21 includes a central processing unit (CPU) and a random access memory (RAM). As controller 21 performs programs stored in data storage unit 29, various functions are achieved. Controller 21 may include a dedicated hardware circuit designed so as to achieve desired functions. In other words, controller 21 may include the CPU, a micro processing unit (MPU), a field-programmable gate array (FPGA), a digital signal processor (DSP), or an application specific integrated circuit (ASIC), for example.

Data storage unit 29 is a recording medium such as a hard disk device, a solid state drive (SSD), or a semiconductor memory. Data storage unit 29 stores programs performed by controller 21, data generated by controller 21, and the like. First to third interfaces 23, 25, 27 are circuits for communication. Movable body communication system 28 is a communication device that acquires driving information about traveling of vehicle 100 (at least one of information such as a travel distance, a driving speed, sudden acceleration, and sudden braking) and transmits the information to a telematics server. Movable body communication system 28 also transmits an analysis result of the image captured by imaging device 10 to the server as the driving information and receives various services that utilize the information.

[1-1-2. Imaging Device]

Figure 3:
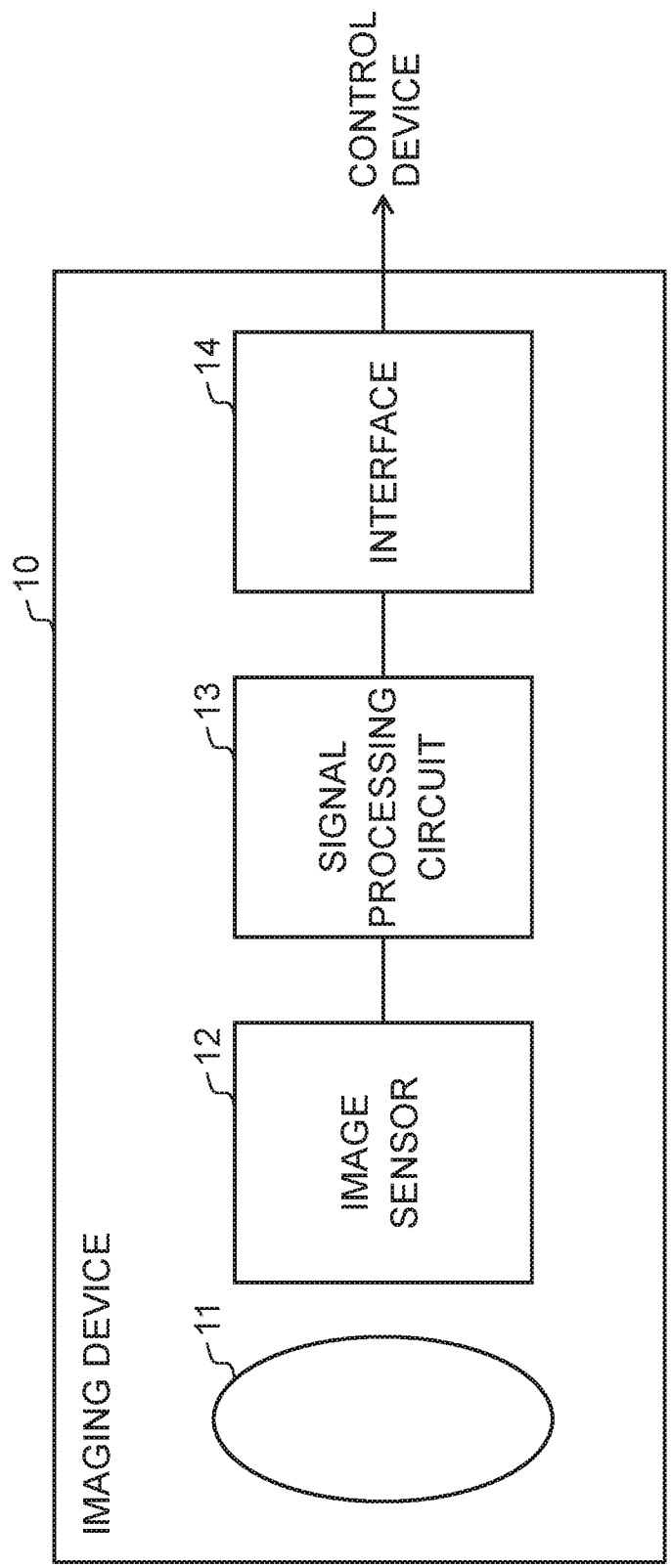
FIG. 3 shows a configuration of an imaging device in the imaging system.

FIG. 3 is a block diagram of a configuration of imaging device 10. As shown in FIG. 3, imaging device 10 includes optical system 11, image sensor 12, signal processing circuit 13, and interface 14. Image sensor 12 captures a subject image generated by receiving light through optical system 11 and generates an image signal. Signal processing circuit 13 performs predetermined image processing (for example, gamma correction and distortion correction) on the image signal. Interface 14 outputs the image signal having been processed by signal processing circuit 13 to an external apparatus.

Optical system 11 is an optical element for forming an image on an imaging surface of image sensor 12. Optical system 11 includes a lens, a diaphragm, and a filter, for example. Optical system 11 will be described later in detail.

Image sensor 12 is an imaging element that converts an optical signal into an electric signal. Image sensor 12 includes an imaging surface on which a plurality of pixels are two-dimensionally arranged at equal intervals. Image sensor 12 may be configured to have sensitivity not only in a visible light region but also in an invisible light region (for example, a near-infrared light region with a wavelength ranging from 0.7 µm to 2.5 µm). That is to say, image sensor 12 includes a group of pixels receiving light in the invisible light region, in addition to a group of pixels receiving RGB light. The wavelength of light received by each pixel of image sensor 12 is selected based on the characteristic of an optical filter arranged on each pixel. Image sensor 12 is a charge coupled device (CCD) image sensor, a complementary metal oxide semiconductor (CMOS) image sensor, or an n-channel metal-oxide semiconductor (NMOS) image sensor, for example.

Signal processing circuit 13 performs predetermined image processing such as gamma correction and distortion correction on the image signal generated by image sensor 12.

Interface 14 is a circuit for transmitting image data from imaging device 10 to control device 20.

Figure 4:
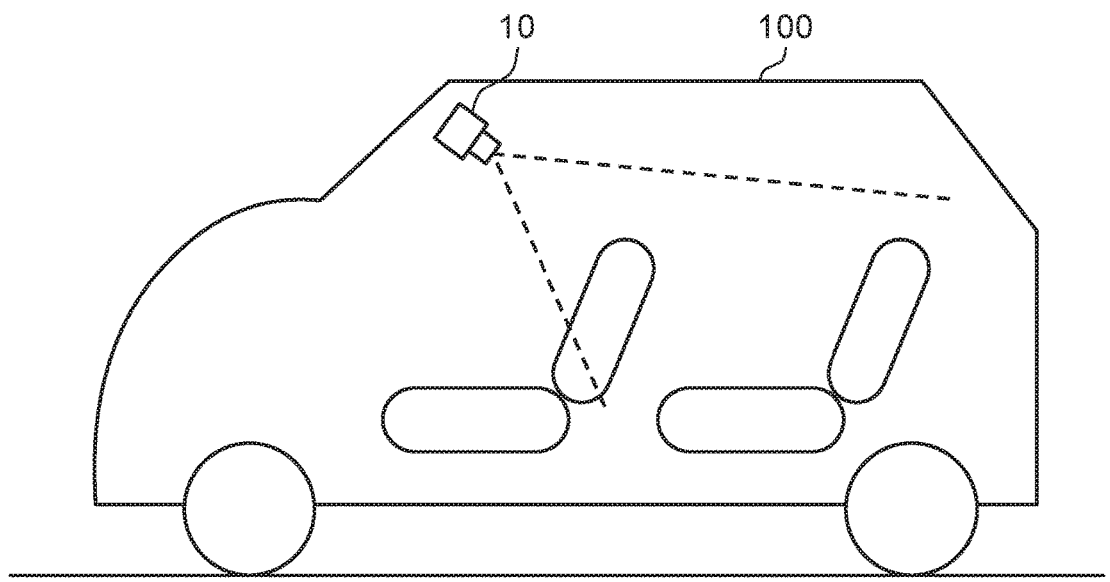
FIG. 4 is an explanatory diagram of a capturing range of the imaging device.
Figure 5:
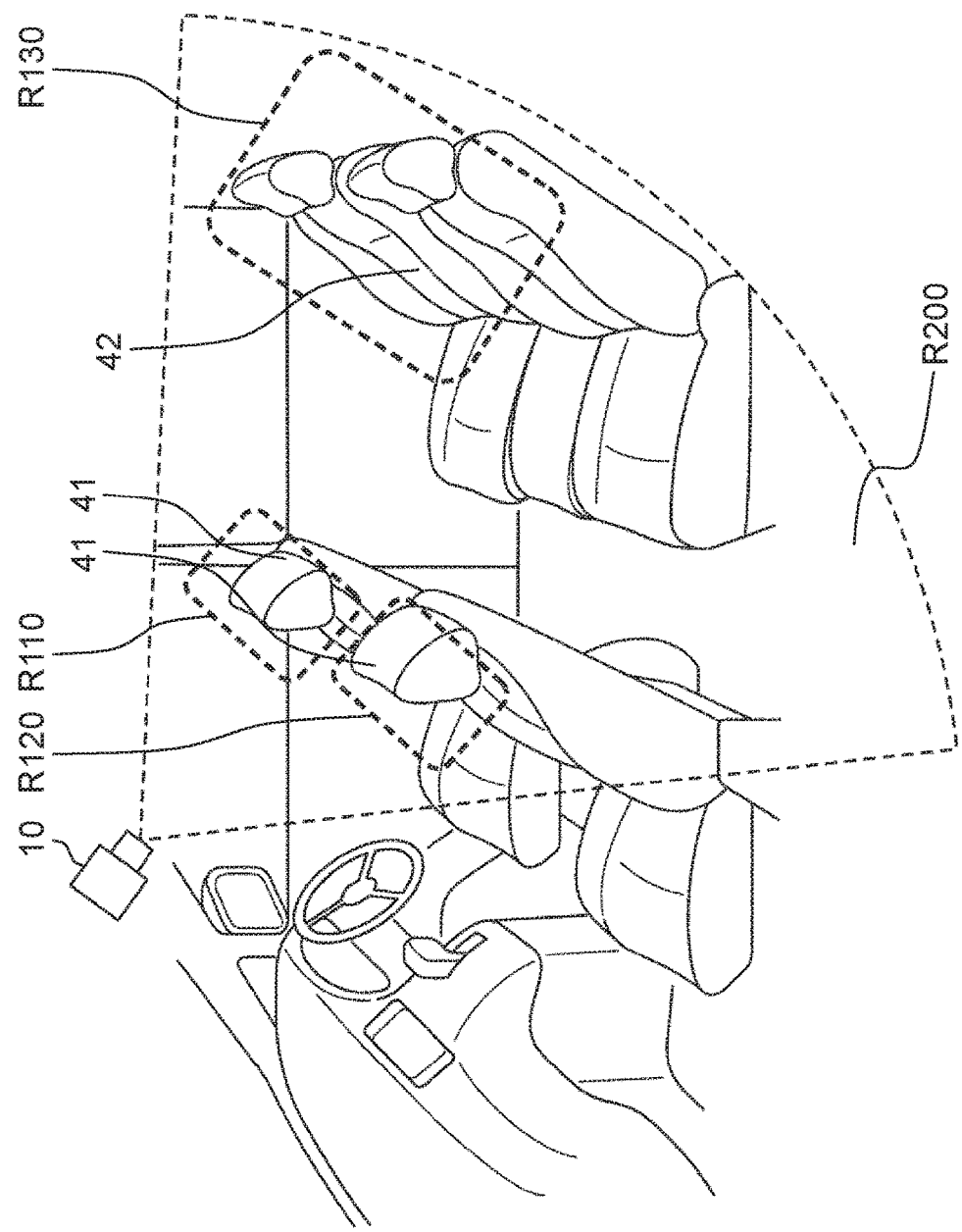
FIG. 5 is an explanatory diagram of a range of a compartment captured by the imaging device.

FIGS. 4 and 5 schematically show a capturing range of imaging device 10 (a subject region). As shown in FIGS. 4 and 5, imaging device 10 is mounted on top of inside of a vehicle, for example, on a ceiling or a room mirror so as to capture an image of the inside of the vehicle. Imaging device 10 is mounted so as to face rear for the purpose of capturing an image of an occupant's face. Imaging device 10 is configured to capture an image of a part of the entire subject region while being magnified. Specifically, imaging device 10 is configured to be capable of capturing an image of a region possibly including an occupant's face at a higher magnification ratio than those of other regions. For example, as shown in FIG. 5, imaging device 10 is capable of capturing images of region R110 including a driver's face, region R120 including a face of a passenger in a passenger seat, and region R130 including a face of an occupant in a rear seat, while being magnified. In particular, region R110 preferably includes driver's eyes. When the driver is not present in the driver seat, region R110 includes headrest 41 of the driver seat. When the passenger is not present in the passenger seat, region R120 includes headrest 41 of the passenger seat. When the occupant is not present in the rear seat, region R130 includes at least one of headrest 41 and backrest 42 of the rear seat.

Figure 6:
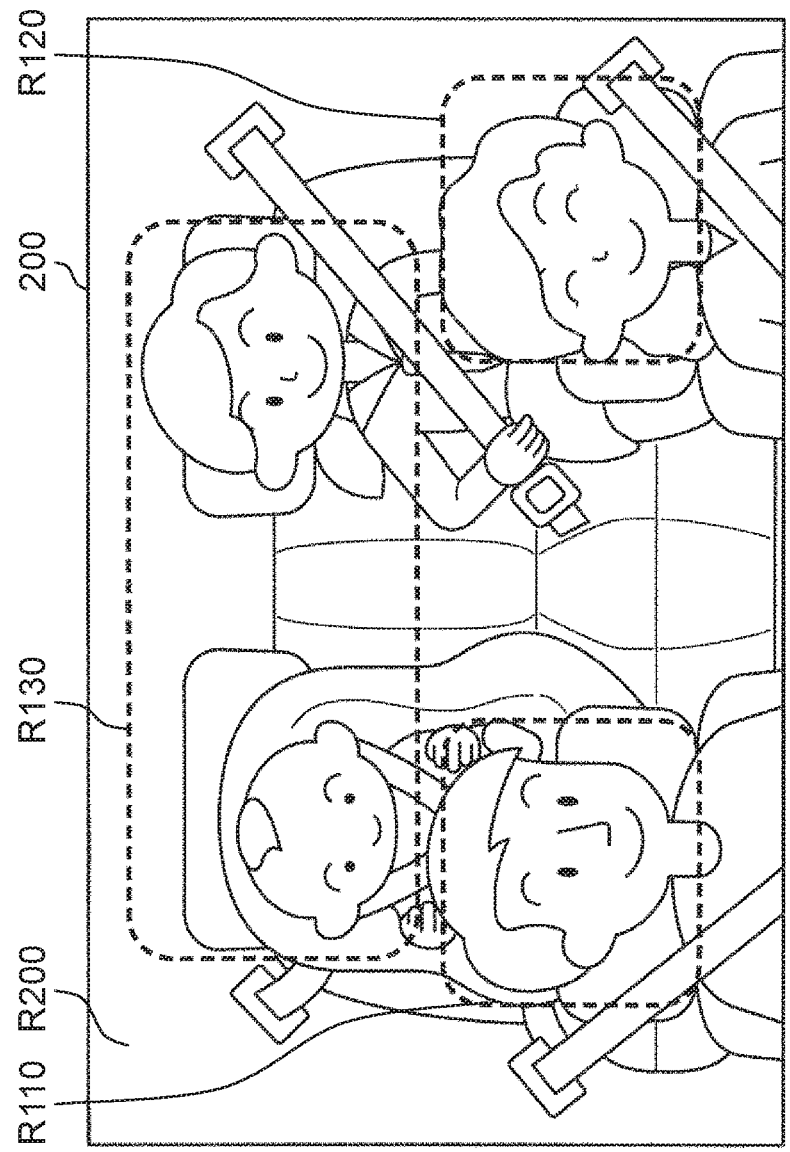
FIG. 6 is an explanatory diagram of an example of a region captured while being magnified, of a subject in the compartment.

FIG. 6 is a specific explanatory diagram of an example of a subject captured by imaging device 10. Imaging device 10 is configured to capture images of region R110 including the face of the driver in the driver seat, region R120 including the face of the passenger in the passenger seat, and region R130 including faces of occupants in the rear seat in subject region 200 captured by imaging device 10 at a higher magnification ratio than that of region R200 except for these regions, as shown in FIG. 6.

Optical system 11 of imaging device 10 has such optical characteristics that the magnification ratio of regions R110 to R130 is larger than that of region R200. Optical system 11 is designed such that the magnification ratio changes not intermittently but successively and monotonically in regions R110 to R130 and region R200 except for regions R110 to R130.

Figure 7:
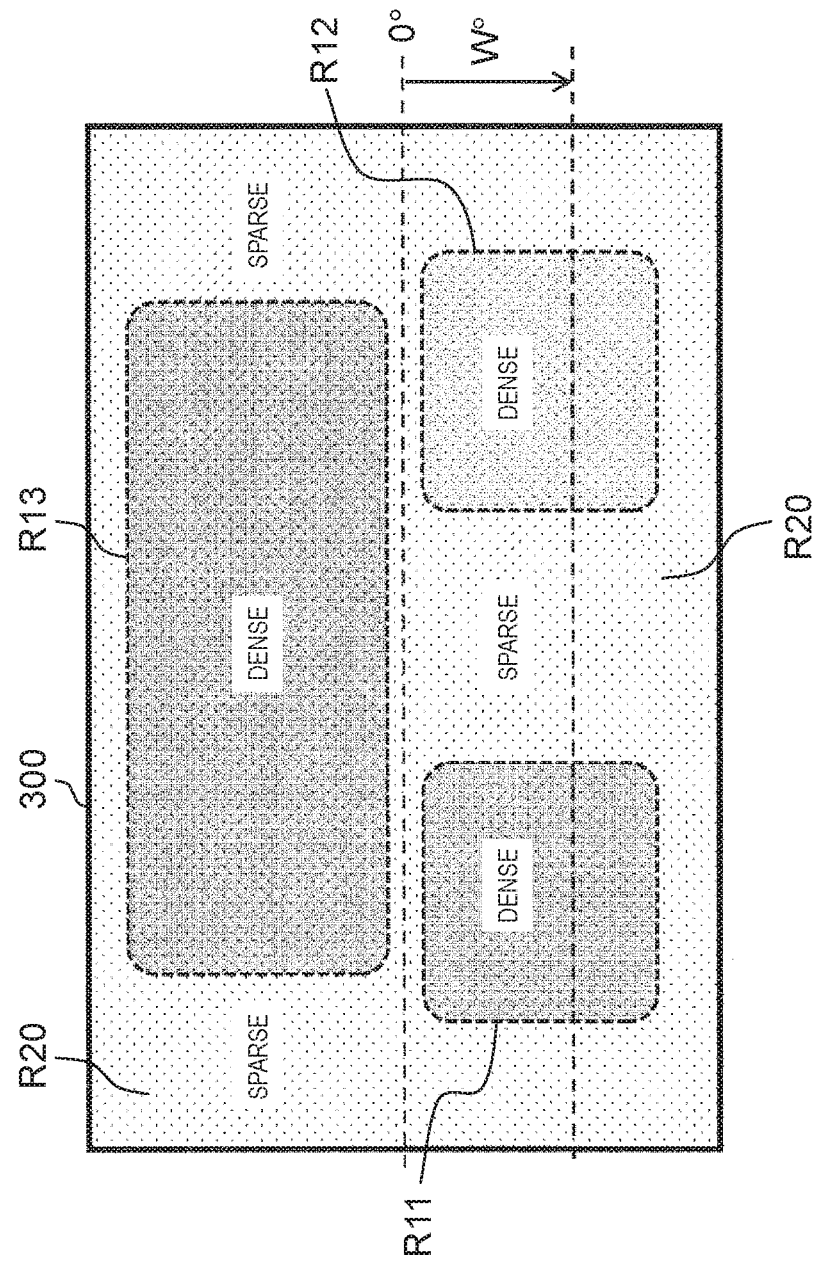
FIG. 7 is an explanatory diagram of a distribution of resolution (magnification ratio) of an image captured by the imaging device.

FIG. 7 is an explanatory diagram of a distribution of a magnification ratio (that is, image resolution) of a captured image formed on an imaging surface of image sensor 12 by optical system 11 of imaging device 10. In captured image 300, region R11 (an example of the first region) corresponds to subject region R110, and region R20 (an example of the second region) corresponds to subject region R200. That is to say, an image of subject region R110 is formed at a relatively large magnification ratio in region R11, whereas an image of subject region R200 is formed at a relatively low magnification ratio in region R20. The magnification ratio of the image in region R11 is relatively higher than the magnification ratio of the image in region R20. Similarly, images of subject regions R120, R130 are formed at a relatively high magnification ratio in regions R12, R13 (an example of the first or third region). The magnification ratio of the images in regions R12 and R13 is relatively higher than the magnification ratio of the image in region R20. The configuration of optical system 11 that achieves these optical characteristics will be specifically described below.

[1-1-2-1. Optical System]

Figure 8:
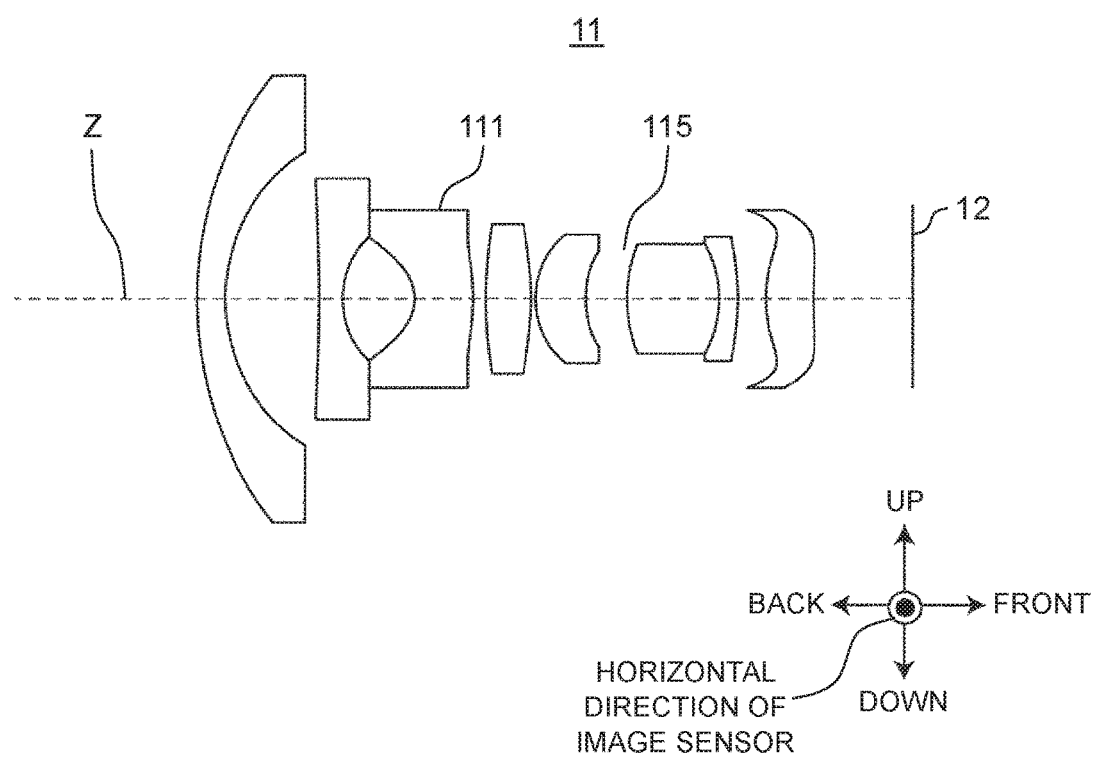
FIG. 8 schematically shows a configuration of an optical system of the imaging device.

FIG. 8 shows a configuration of optical system 11 of imaging device 10. FIG. 8 shows a cross-section when optical system 11 is virtually cut by a vertical plane including optical axis Z (a plane in which a horizontal direction of the image sensor is a normal). Optical axis Z is a virtual line that passes through a center of an imaging surface of image sensor 12 and orthogonally intersects the imaging surface. When optical system 11 includes, for example, a mirror or a prism that reflects light, its optical axis is bent by reflection. As shown in FIG. 8, optical system 11 includes a plurality of lenses and diaphragm 115. In particular, optical system 11 includes free-form lens 111 for the purpose of achieving the optical characteristics described above.

The free-form lens is a lens in which a surface for refracting light to form an image has a non-arc shape and is not rotation symmetry. In the present disclosure, a cylindrical lens is also defined as a type of an arc lens. That is to say, the cylindrical lens is defined as a lens different from the free-form lens in the present disclosure. The free-form lens has the non-arc shape that is not a part of a perfect circle. Materials of the free-form lens include, but are not particularly limited to, glass, resin, and the like. Examples of a method of manufacturing the free-form lens include, but are not particularly limited to, a method of molding the free-form lens using a mold such as a metal mold.

Free-form lens 111 is capable of freely varying the magnification ratio of an image to be formed based on at least one of a horizontal view angle and a vertical view angle. Free-form lens 111 is designed such that in captured image 300, the magnification ratio of some regions R11 to R13 is higher than that of region R20 except for regions R11 to R13, as shown in FIG. 7. Regions R11 to R13 with a high magnification ratio are appropriately arranged so as to correspond to a region including an image analysis target. In the present exemplary embodiment, for example, the positions of regions R1 to R13 are set to respectively correspond to possible positions of faces of occupants in a vehicle.

Image sensor 12 according to the present exemplary embodiment has a uniform pixel distribution in the horizontal and vertical directions. The resolution of an image formed on the imaging surface of image sensor 12 by optical system 11 of imaging device 10 is thus shown in FIG. 7. That is to say, in captured image 300, the image resolution in regions R11 to R13 with a high magnification ratio is high (dense), whereas the image resolution in region R20 except for regions R11 to R13 is relatively low (sparse). In the present exemplary embodiment, images of regions R11 to R13 with high resolution are used for image analysis, which improves precision of analysis.

The image resolution is described. In the present exemplary embodiment, the image resolution is defined as the number of pixels (the number of pixels per unit view angle) of image sensor 12 used for capturing an image with a unit view angle, the image being formed on image sensor 12 through optical system 11. The resolution is defined by the following formula.

$$\text{Resolution} = \text{number of pixels required to capture image with predetermined view angle/predetermined view angle} \quad (1)$$

Figure 9:
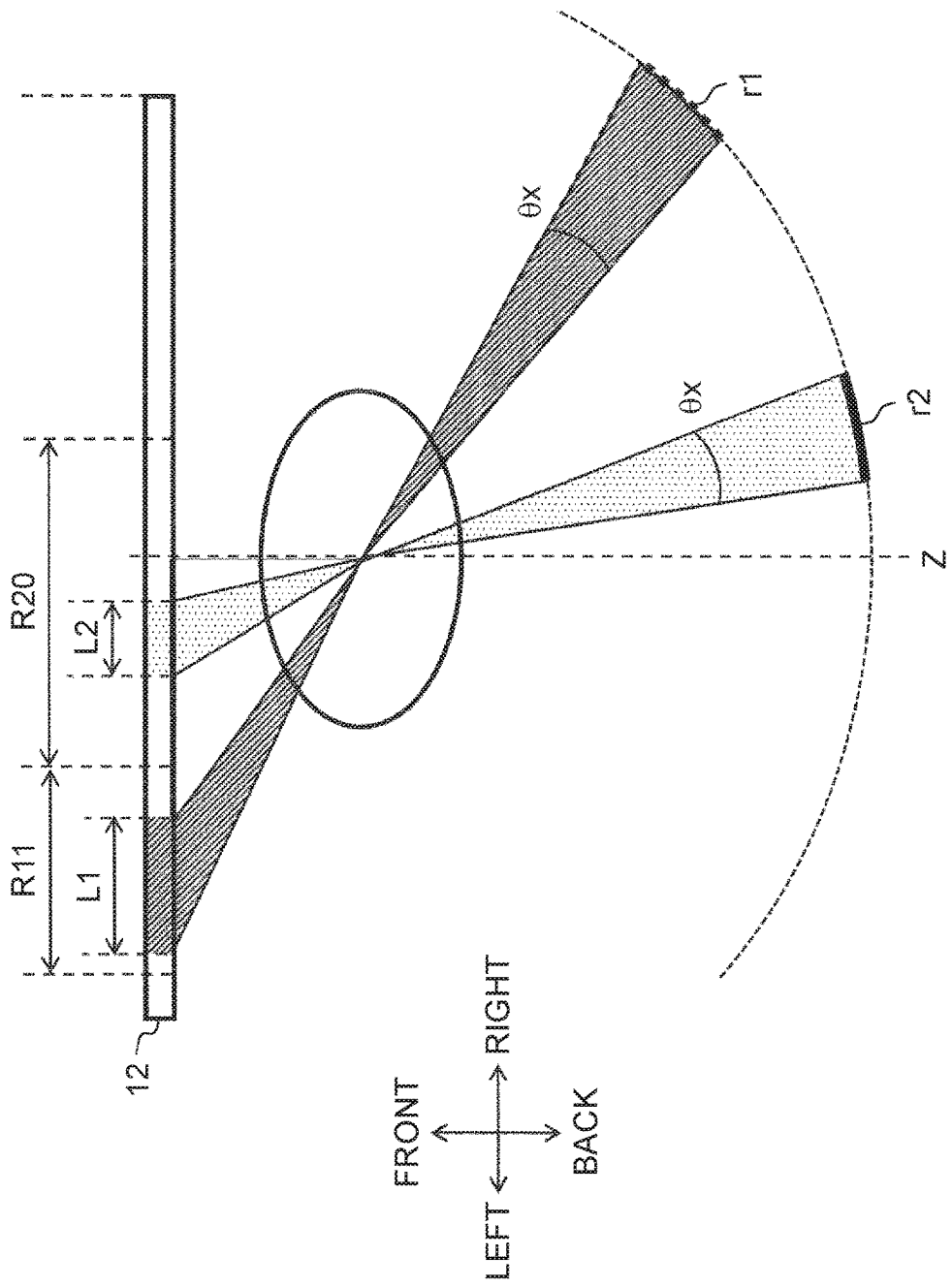
FIG. 9 is an explanatory diagram of the resolution of an image formed on an image sensor by the optical system of the imaging device.

The resolution of an image formed by optical system 11 is specifically described with reference to FIG. 9. FIG. 9 is a schematic explanatory diagram of an imaging state on image sensor 12 when virtually cut by a predetermined cross-section. The predetermined cross-section is a horizontal plane including optical axis Z that is inclined vertically and downward by view angle W°. View angle W° is set such that the cross-section includes region R11, region R12, and region R20 (see FIG. 7). As shown in FIG. 9, it is considered that a subject image in first region r1 in a range of view angle θx and a subject image in second region r2 having identical view angle θx are formed onto image sensor 12 through optical system 11. Region r1 is a part of subject region R110 and corresponds to a part of region R11 in a captured image. Region r2 is a part of subject region R200 and corresponds to a part of region R20 in the captured image.

Optical system 11 is designed such that magnification ratio M1 of region R11 is relatively high whereas magnification ratio M2 of region R20 is relatively low in captured image 300. When image sensor 12 captures an image of a subject in first region r1 through optical system 11, the image in first region r1 is formed on the imaging surface of image sensor 12 while being magnified with magnification ratio M1, as shown in FIG. 9. When image sensor 12 captures an image of a subject in second region r2, the image is formed on the imaging surface of image sensor 12 while being magnified with magnification ratio M2 that is lower than magnification ratio M1. Therefore, length L2 of the image in second region r2 on the imaging surface is less than length L1 of the image in first region r1.

Pixels are two-dimensionally arranged on image sensor 12 at equal intervals. Consequently, as the horizontal length of an image increases, the number of pixels required to capture the image also increases. In other words, number N1 of pixels that are included in a range of length L1 and required to capture the image in first region r1 is larger than number N2 of pixels that are included in a range of length L2 (<L1) and required to capture the image in second region r2. View angle (θx) of first region r1 is equal to view angle (θx) of second region r2. Accordingly, the resolution of the image in first region r1 (=N1/θx) is higher than the resolution of the image in second region r2 (=N2/θx). The image in first region r1 is formed at a location on the imaging surface of image sensor 12 corresponding to region R11. The image in second region r2 is formed at a location on the imaging surface of image sensor 12 corresponding to region R20. The resolution of the image in region R11 is higher than the resolution of the image in region R20. Similarly, the resolution of the images in region R12 and region R13 is higher than the resolution of the image in region R20.

Figure 10:
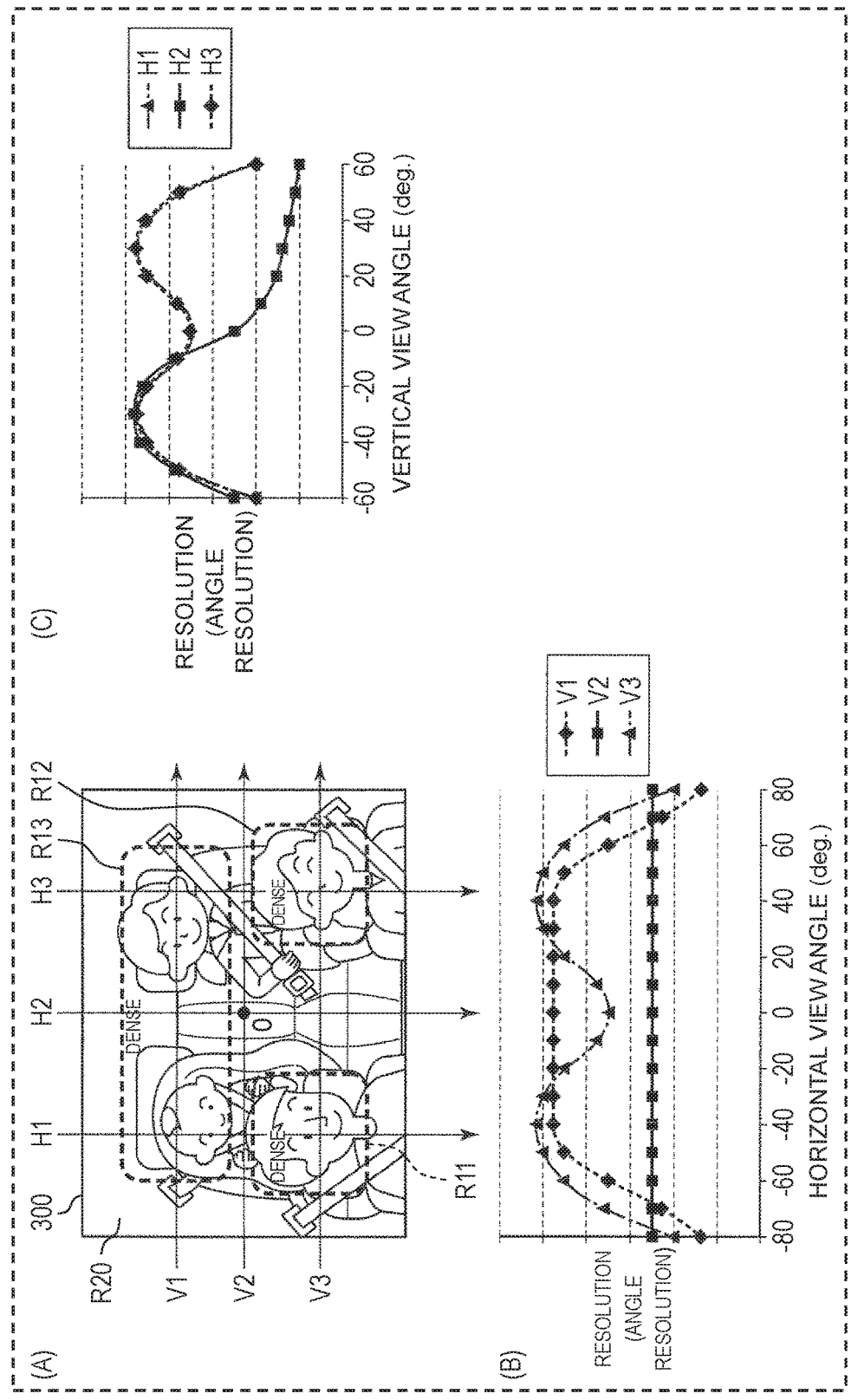
FIG. 10 shows resolution (angle resolution) characteristics of a free-form lens used for the optical system of the imaging device.

FIGS. 10(A) to 10(C) show resolution (angle resolution) characteristics with respect to vertical and horizontal view angles in optical system 11 of imaging device 10. As shown in part (A) of FIG. 10, a center of the vertical and horizontal view angles is 0°. Optical axis Z passes through the center of the view angle. The horizontal view angle ranges from −80° to +80° whereas the vertical view angle ranges from −60° to +60°. Part (B) of FIG. 10 shows the resolution characteristics with respect to the horizontal view angle at a vertical view angle of V1, V2, V3. Part (C) of FIG. 10 shows the resolution characteristics with respect to the vertical view angle at a horizontal view angle of H1, H2, H3.

In examining the resolution characteristics with respect to the horizontal view angle at a vertical view angle of V1 with reference to part (B) of FIG. 10, for example, it is found that the resolution of region R13 with a horizontal view angle ranging from −50° to +50° is higher than the resolution of region R20. When the vertical view angle is V2, regions R11 to R13 with high resolution do not appear, and thus the resolution is fixed and low regardless of the horizontal view angle. When the vertical view angle is V3, the resolution is high in region R11 with a horizontal view angle ranging from −60° to −20° and in region R12 with a horizontal view angle ranging from 20° to 60°.

In examining the resolution characteristics with respect to the vertical view angle at a horizontal view angle of H1 or H3 with reference to part (C) of FIG. 10, the resolution is high in region R13 with a vertical view angle ranging from −50° to −10° and in region R11 or R12 with a vertical view angle ranging from 10° to 50°. In examining the resolution characteristics with respect to the vertical view angle at a horizontal view angle of H2, the resolution is high in region R13 with a vertical view angle ranging from −50° to −10° and is low in region R20.

[1-2. Operation]

Operations of imaging device 10 and control device 20 configured as described above will be described below.

Imaging device 10 shown in FIG. 1 captures an image of inside of vehicle 100 while vehicle 100 is travelling or vehicle 100 stops, generates image data, and transmits the image data to control device 20. Imaging device 10 generates a visible light image and an invisible light (for example, near-infrared light) image.

Control device 20 shown in FIG. 2 receives the image data through first interface 23. Controller 21 of control device 20 performs image analysis (sensing) on the image data received from imaging device 10 to acquire various information about a state of the inside of the vehicle. Specifically, controller 21 analyzes at least one of images of regions R11, R12, and R13 shown in FIG. 7 in captured image 300. As regions R11 to R13 have high resolution, controller 21 can perform analysis with high precision using these images. For example, by analyzing the image of region R11 during travelling of the vehicle, controller 21 can determine a state of a driver, for example, an awakening state of the driver. When the driver does not awake, for example, controller 21 can output a predetermined signal. By analyzing the images of regions R12 and R13, controller 21 can also determine whether an occupant is present in the vehicle. This result of determination is useful for preventing a child from being left in the vehicle, for example. When a child is left in the vehicle, controller 21 can output a predetermined signal, for example.

When it is assumed that precision of sensing may be degraded by surrounding environments including a case where a sufficient amount of light cannot be obtained in the vehicle only by visible light and a case where disturbance of ambient light significantly affects sensing, controller 21 can perform image analysis using an image generated by receiving invisible light. That is to say, controller 21 can perform image analysis using an image generated by receiving invisible light. An image captured using visible light and an image captured using invisible light may be simultaneously generated in imaging device 10 or may be independently generated in imaging device 10. Controller 21 can reduce influence of surrounding environments such as the case where a sufficient amount of light cannot be obtained in the vehicle only by visible light, thus performing image analysis with high precision. By using wavelengths in the near-infrared region, controller 21 can sense vital signs such as blood flow or a pulse, and thus obtain information of a detection target more accurately.

Controller 21 generates a control signal of control target 60 based on a result of image analysis and transmits the control signal via third interface 27 to control target 60. Control target 60 is then controlled based on the state of the inside of the vehicle.

For example, by performing image analysis on region R11 in a captured image, controller 21 can determine an awakening state or a health state of the driver, determine whether a driving mode needs to be switched from a manual mode to a self-driving mode, and control switching based on a result of determination. More specifically, controller 21 analyzes an image of eyes in the image of region R11. For example, controller 21 can detect information indicating a number of blinks or a trajectory of a pupil from a change in image data of eyes. When the awakening state or the health state of the driver is below a predetermined reference level suitable for driving, controller 21 can switch the driving mode from the manual driving mode to the self-driving mode. In the present exemplary embodiment, the resolution of region R11 where the image of the eyes is formed is higher than the resolution of region R20, and thus controller 21 can analyze the image of the eyes with high precision.

Controller 21 of control device 20 may perform predetermined image processing on the received image data, generate image data for display, and transmit the image data for display via second interface 25 to display 30. For example, controller 21 may cut out the images of regions R11 to R13 with high resolution, resize the images to a size suitable for display, and generate the image data for display. Display 30 displays an image based on the image data received from control device 20. The driver of vehicle 100 checks the image displayed on display 30, thus learning the state of the inside of the vehicle.

Controller 21 may also transmit a result of image analysis to movable body communication system 28. Movable body communication system 28 may transmit the result of image analysis to a telematics cloud server. Driver information may be stored as telematics in the server and be shared. The server may predict behavior of a driver and use a result of analysis for preventing accidents or for telematics insurance. That is to say, images of a driver of a long-distance truck or a bus may be analyzed with high precision and a result of analysis may be provided from the server to a driver management division. The driver management division can thus learn the awakening state or the health state of the driver and use such information for preventing accidents. As a result, it is possible to reduce costs of accidents borne by a driver or a company hiring the driver and prevent a decrease in social reliability. By using such information, it is possible to manage characteristics of drivers that may lead to dangerous driving even if an accident does not occur in practice, and the information is also used to educate drivers.

Imaging device 10 according to the present exemplary embodiment can capture an image of the inside of a vehicle with a wide range of the view angle and capture an image in a partial region that is important for sensing with high resolution, thus improving the precision of analysis.

[1-3. Effects and Others]

As described above, imaging device 10 according to the present exemplary embodiment shown in FIG. 3 (an example of an imaging device) includes image sensor 12 and optical system 11. Image sensor 12 includes an imaging surface on which a plurality of pixels are two-dimensionally arranged.

Image sensor 12 generates image data from a subject image formed on the imaging surface. The number of pixels used for capturing a subject image included in a unit view angle is defined as resolution. The imaging surface includes a first region (for example, at least one of regions R11, R12, and R13 shown in FIG. 7) and a second region different from the first region (for example, region R20 shown in FIG. 7). Optical system 11 forms the subject image on the imaging surface such that the resolution of a first subject image of the subject image in the first region is higher than the resolution of a second subject image of the subject image in the second region. Regions R11 to R13 with high resolution are arranged so as to include regions where an image of a person's face is formed on the imaging surface.

With the configuration described above, the resolution of regions R11 to R13 in a captured image is thus higher than the resolution of region R20. Consequently, it is possible to achieve a wide view angle as a whole. Meanwhile, imaging device 10 can capture an image in which a region required for image analysis has high resolution. It is thus possible to improve the precision of analyzing a captured image. In the present exemplary embodiment, regions R11 to R13 with high resolution are particularly arranged so as to include regions where an image of a person's face is formed on the imaging surface. It is thus possible to improve the precision of analysis based on an image of parts of a person's face.

Optical system 11 may also include free-form lens 111. Optical system 11 is thus freely designed such that a magnification ratio changes depending on a view angle.

The imaging surface may also include a third region different from the first and second regions. Optical system 11 may form a subject image on the imaging surface such that the resolution of a third subject image of the subject image in the third region is higher than the resolution of the second subject image of the subject image in the second region. The first region is at least one of regions R11, R12, and R13, and may be, for example, region R11. The third region is at least one of regions R11, R12, and R13, and may be, for example, region R13. In this case, the first subject image includes a driver's face and the third subject image includes a child's face in a rear seat, for example. The imaging surface may include a plurality of regions with high resolution. It is thus possible to analyze images of a plurality of regions in the vehicle with high precision.

When a plurality of regions with high resolution are included in the imaging surface, resolutions of the regions may be different from each other. That is to say, it is only required that in optical system 11, a magnification ratio is designed based on an imaging region. When assuming a case where a user has to analyze the awakening state or the health state of a driver with high precision, and at the same time, has to determine whether a child sits in the rear seat, in some cases, the resolution of region R13 may be lower than that of region R11. In those cases, the resolution of region R13 may be designed to be higher than the resolution of region R20 but lower than the resolution of region R11.

When a plurality of regions with high resolution are included in the imaging surface, sizes of the regions may be different from each other. For example, region R11 may be smaller in size than region R13. By setting the size of a region based on a subject image to be subjected to image analysis, it is possible to rationally perform image analysis.

When a plurality of high-resolution regions are arranged on the imaging surface in at least one of a horizontal direction and a vertical direction, the resolution of a region between the high-resolution regions may be higher than the resolution of a low-resolution region. That is to say, the resolution of a region between region R11 and region R12 may be higher than average resolution of region R20. By moderating a change in the magnification ratio of optical system 11, distortion of optical system 11 can be reduced.

When imaging device 10 is placed in the vehicle, the high-resolution region may include region R11 where an image of a driver's face is captured and region R12 where an image of a passenger in a passenger seat is captured. The identical imaging device 10 can be used for both a right-hand drive vehicle and a left-hand drive vehicle.

When there are no occupants in the vehicle, an image of headrest 41 of a driver seat may be captured in region R11, an image of headrest 41 of a passenger seat may be captured in region R12, and an image of backrest 42 of a rear seat may be captured in region R13. For example, an image of occupant's eyes is thus formed in region R11 and region R12 with high precision. An image of a child is easily formed in region R13.

Image sensor 12 may be capable of receiving light in the visible light region and in the invisible light region. If imaging device 10 is placed in a dark environment, it is possible to achieve image analysis with high precision by imaging light in the invisible light region.

Imaging device 10 may also configure an imaging system with control device 20. The control device analyzes image data generated by imaging device 10. Control device 20 analyzes an image formed in a high-resolution region (for example, at least one of regions R11, R12, and R13), in the image indicated by the image data.

(Second Exemplary Embodiment)

Optical system 11 is constituted by a free-form lens in the first exemplary embodiment for the purpose of generating a captured image in which some regions R11 to R13 have high resolution. However, it is not necessary for optical system 11 to have the free-form lens in order to generate such a captured image. The captured image can be achieved by modifying a pixel distribution of image sensor 12 with a common, rotational symmetric optical system. A configuration of imaging device 10 that includes an optical system without a free-form lens will be described below.

Figure 11:
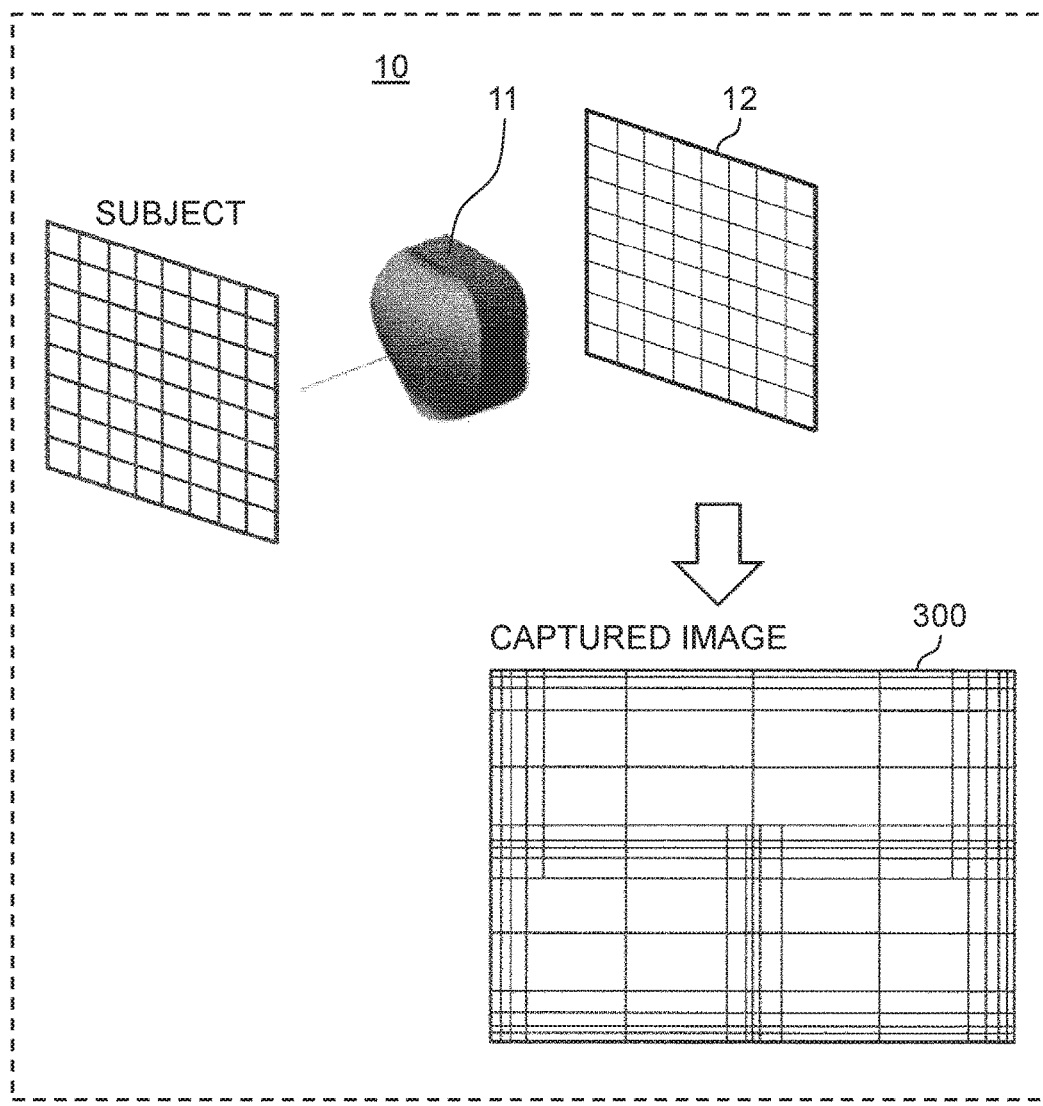
FIG. 11 shows the optical system and the image sensor in the imaging device according to a first exemplary embodiment.
Figure 12:
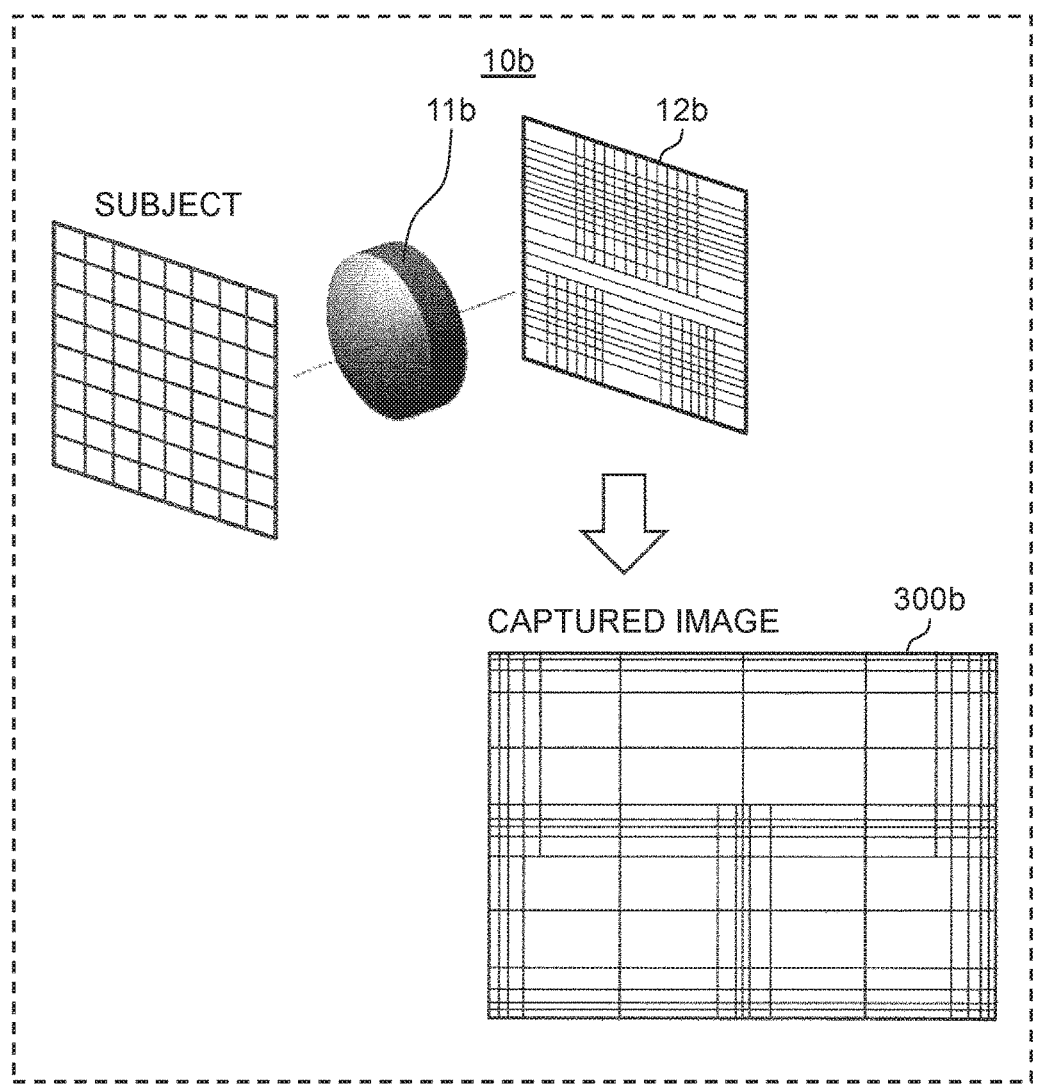
FIG. 12 shows an optical system and an image sensor in an imaging device according to a second exemplary embodiment.

FIG. 11 is an explanatory diagram of a pixel distribution of image sensor 12 in imaging device 10 according to the first exemplary embodiment and a resolution distribution of captured image 300 captured by a combination of optical system 11 and image sensor 12. FIG. 12 is an explanatory diagram of a pixel distribution of image sensor 12b in imaging device 10b according to the second exemplary embodiment and a resolution distribution of captured image 300b captured by a combination of optical system 11b and image sensor 12b.

As shown in FIG. 11, a plurality of pixels are two-dimensionally arranged on an imaging surface of image sensor 12 at equal intervals in the first exemplary embodiment. An image of a certain region (for example, region R11) with high resolution is formed on the imaging surface of image sensor 12 by using free-form lens 111 of optical system 11. It is thus possible to obtain a captured image in which region R11 has high resolution and other regions have low resolution.

Figure 13:
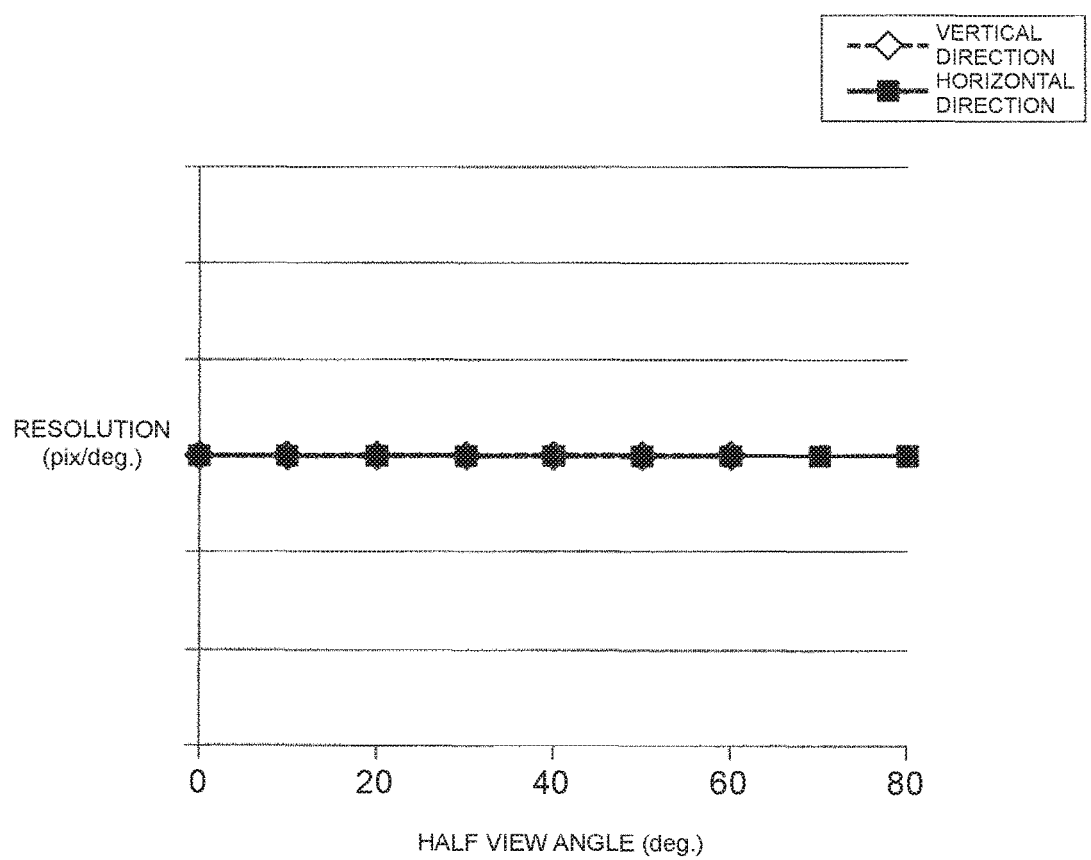
FIG. 13 shows resolution characteristics of the optical system in the imaging device according to the second exemplary embodiment.

Meanwhile, in the present exemplary embodiment, imaging device 10b includes optical system 11b that is a rotational symmetric lens and image sensor 12b with a specific pixel distribution, as shown in FIG. 12. Optical system 11b is a lens that has resolution (angle resolution) characteristics shown in FIG. 13 with respect to vertical and horizontal resolutions when an image is formed on an image sensor with a uniform pixel distribution. That is to say, optical system 11b has a uniform magnification ratio with respect to vertical and horizontal view angles.

Figure 14:
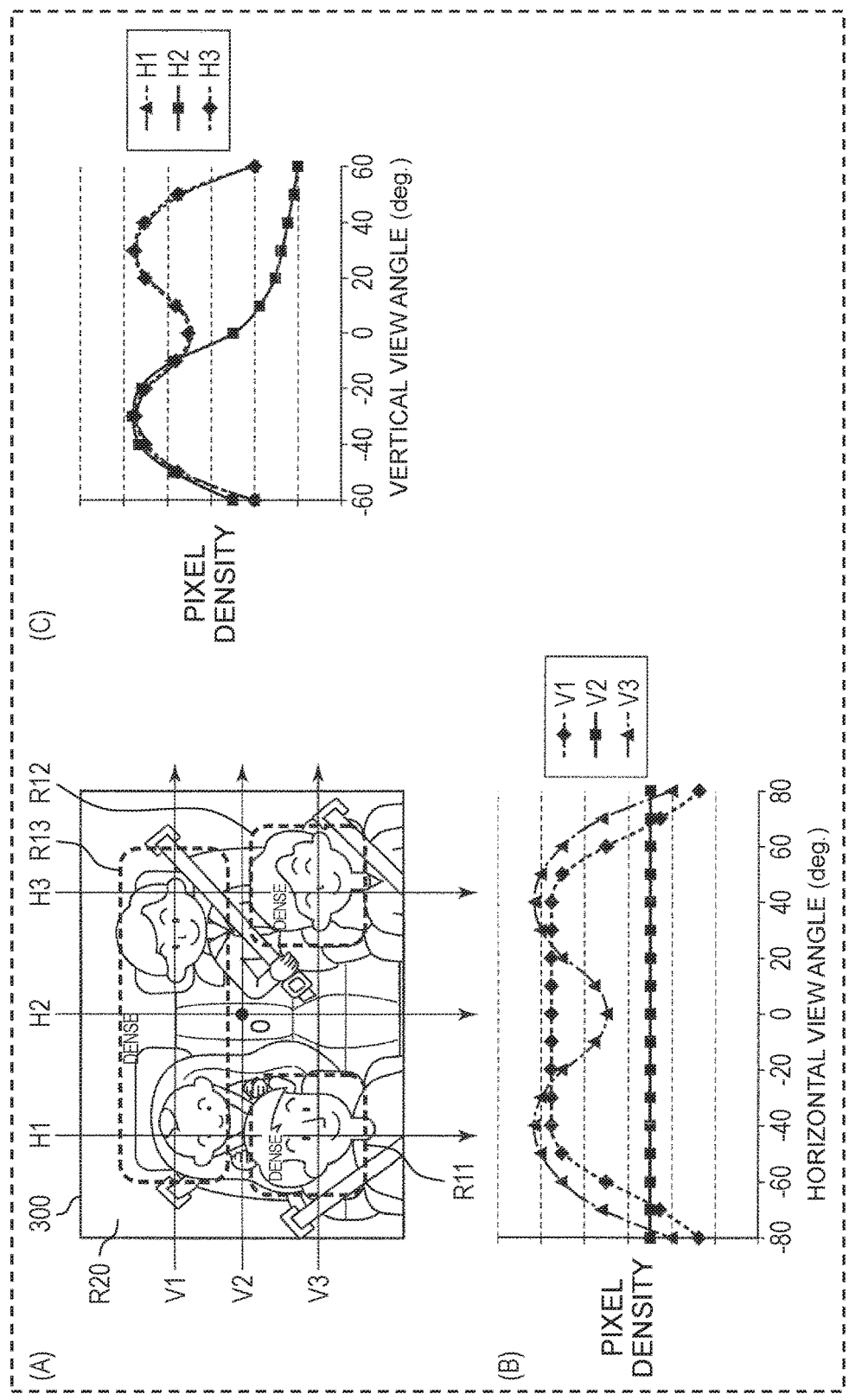
FIG. 14 shows pixel density of the image sensor in the imaging device according to the second exemplary embodiment.

FIGS. 14(A) to 14(C) are explanatory diagrams of a pixel density distribution with respect to vertical and horizontal view angles in image sensor 12b according to the second exemplary embodiment. As shown in part (A) of FIG. 14, a center of the vertical and horizontal view angles is 0°. Optical axis Z passes through the center of the view angle. The horizontal view angle ranges from −80° to +80° whereas the vertical view angle ranges from −60° to +60°. Part (B) of FIG. 14 shows the pixel density distribution of image sensor 12b with respect to the horizontal view angle at a vertical view angle of V1, V2, V3. Part (C) of FIG. 14 shows the pixel density distribution of image sensor 12b with respect to the vertical view angle at a horizontal view angle of H1, H2, H3.

As shown in parts (B) and (C) of FIG. 14, image sensor 12b has such a pixel density distribution that regions corresponding to regions R11 to R13 have a high pixel density and a region other than regions R11 to R13 (a region corresponding to region R20) has a low pixel density.

By using the combination of optical system 11b and image sensor 12b with the characteristics described above, it is possible to generate captured image 300b that has a similar resolution distribution to the first exemplary embodiment.

As described above, imaging device 10b according to the present exemplary embodiment includes image sensor 12b that has an imaging surface on which a plurality of pixels are two-dimensionally arranged and that generates image data from a subject image formed on the imaging surface and optical system 11b that images a subject in a predetermined range of the vertical view angle and in a predetermined range of the horizontal view angle on the imaging surface of image sensor 12b. The imaging surface includes a first region (for example, at least one of regions corresponding to regions R11, R12, and R13) and a second region different from the first region (for example, region R20). The number of pixels used for capturing a subject image included in a unit view angle is defined as resolution. Optical system 11b forms an image on the imaging surface with a uniform magnification ratio. Image sensor 12b has such a pixel distribution that the pixel density of at least one first region is higher than the pixel density of at least one second region. A region with a high pixel density is arranged so as to include a region where an image of a person's face is formed.

With the configuration described above, the resolution of regions R11, R12, and R13 in a captured image is higher than the resolution of region R20, as in the first exemplary embodiment. It is thus possible to improve the resolution of a part required for image analysis, while achieving a wide view angle as a whole. It is thus possible to improve the precision of analyzing a captured image. In particular, regions R11 to R13 with high resolution are arranged so as to include a region where an image of a person's face is formed and thus it is possible to improve the precision of analysis based on an image of parts of a person's face.

(Other Exemplary Embodiments)

The first and second exemplary embodiments have been described above as examples of the technique disclosed in the present application. However, the technique according to the present disclosure is not limited to the first and second exemplary embodiments, but is applicable to other exemplary embodiments including appropriate modifications, replacements, additions, omissions, and the like. In addition, new exemplary embodiments can be made by combining constituent elements described in the first and second exemplary embodiments. Hence, other exemplary embodiments are described below.

In the exemplary embodiments described above, the electronic room mirror and the in-vehicle display are exemplified as the display device. However, a type of the display device is not limited to these electronic room mirror and in-vehicle display. An idea of the present disclosure can be adapted to display systems that use various types of display devices according to uses (for example, a head-up display).

While regions with high resolution or with a high pixel density (regions R11 to R13) are determined based on the position where an image of a person's face is formed in the exemplary embodiments described above, a region determination method is not limited to that case. The size, position, and number of regions with high resolution or with a high pixel density may be appropriately determined based on a target (an object or an event) to be analyzed.

While signal processing circuit 13 performs the gamma correction and the distortion correction on images in the exemplary embodiments described above, control device 20 may perform these processing.

While vehicle 100 of an automobile with two rows of seats has been described as an example of a movable body in the exemplary embodiments described above, the movable body is not limited to vehicle 100. The imaging device according to the exemplary embodiments described above may be used for other movable bodies.

The movable body may be, for example, a large vehicle such as a bus with a plurality of rows of seats. In this case, as shown in FIG. 15, an optical system or an image sensor may be designed such that the resolution (that is, magnification ratio) of region R31 including columns of seats from front to back in captured image 300 of the inside of the vehicle is higher than the resolution of region R32, for example.

The movable body may also be a railway vehicle. In this case, as shown in FIG. 16, the resolution of region R31 including an entrance and exit in captured image 300 may be higher than the resolution of region R32, for example. An imaging system can thus analyze an image of passengers getting on and off the vehicle with high precision.

The movable body may also be an airplane. In this case, as shown in FIG. 17, the resolution of region R51 including rows of seats in a cabin of the airplane in captured image 300 may be higher than the resolution of region R52, for example. The imaging system can thus analyze an image of occupants in the airplane with high precision. As shown in FIG. 18, imaging device 10 may be placed in a cockpit for the purpose of capturing an image of a region including a pilot's face from front of the pilot. In this case, the resolution (that is, magnification ratio) of a region corresponding to subject region R610 including the pilot in a captured image may be higher than the resolution of a region corresponding to subject region R620 except for subject region R610. It is thus possible to analyze a part of the captured image including the image of the pilot with high precision. As a result, an analyzer can recognize a state of the pilot with high precision.

The movable body may also be a ship. The imaging device may capture at least one of an image of a cabin of the ship or an image of a cockpit of the ship. The movable body may also be a constructional machine (for example, a crane) or may be an agricultural machine (for example, a combine).

The size and position of a region with relatively high resolution (that is, relatively high magnification ratio) are only illustrative in the exemplary embodiments described above. The size and position of the region with relatively high resolution (that is, relatively high magnification ratio) may be appropriately determined based on the purpose of image analysis or display.

Numeral values of the view angle, the number of pixels, and the like described in the exemplary embodiments are only examples.

While the free-form lens is used in the optical system in the exemplary embodiments described above, other types of lens whose magnification ratio (that is, resolution) can be freely designed according to a view angle may be used instead of the free-form lens.

While the imaging device is used for the purpose of capturing an image of a state of the inside of the movable body (for example, an automobile) in the exemplary embodiments described above, the purpose of using the imaging device according to the present disclosure is not limited to that case. For example, the imaging device according to the present disclosure may be used as a monitoring camera.

The monitoring camera used as the imaging device according to the present disclosure may be installed in a store. In that case, an optical system of the monitoring camera is designed such that a region corresponding to a movement range of customers in a captured image has high resolution. It is thus possible to capture an image of the movement range of customers with high resolution and to analyze a traffic line of an identical customer using the image of the monitoring camera with high precision. It is thus expected to efficiently promote sales and reduce lost sales.

The imaging device according to the present disclosure may also be used as a monitoring camera in a face recognition system for the purpose of preventing shoplifting and loitering. An optical system of the monitoring camera is designed such that a region including store shelves in a captured image has high resolution. The monitoring camera used as the imaging device according to the present disclosure may be installed in a store, for example. Facial image information extracted from the image captured by the monitoring camera may be matched against face information registered in advance, and an alert may be output to store staff. In this case, it is possible to increase the resolution of an image of a person captured by the monitoring camera, thus increasing the precision of matching.

The imaging device according to the present disclosure may also be used as a monitoring camera in a traffic line analyzing system. An optical system of the monitoring camera is designed such that a region corresponding to a working range of workers in plants or distribution warehouses in a captured image has high resolution. The monitoring camera is installed in plants or distribution warehouses. As the image of the working range of workers has high resolution, the imaging system can collect traffic line information of an identical worker and analyze the working time or the movement distance of the identical worker with high precision. It is thus possible to enhance operation efficiency.

The exemplary embodiments have been described as examples of the technique in the present disclosure. The accompanying drawings and the detailed description have been provided for this purpose.

Accordingly, the constituent elements described in the accompanying drawings and the detailed description may not only include constituent elements that are essential for solving the problems, but may also include constituent elements that are not essential for solving the problems in order to illustrate the technique. It should not be therefore determined that the unessential constituent elements in the accompanying drawings and the detailed description are essential only based on the fact that these constituent elements are included in the drawings and the description.

The above exemplary embodiments are provided to exemplify the technique according to the present disclosure, and thus various changes, replacements, additions, omissions, and the like can be made within the scope of the claims and equivalents thereof.

The imaging device according to the present disclosure can achieve a wide view angle as a whole, and at the same time and capture an image in which a part required for image analysis (for example, a person's face) has high resolution, thus improving the precision of analyzing the captured image. The imaging device according to the present disclosure can thus be used for a device that captures an image of the inside of a movable body (for example, an automobile, a railway vehicle, an airplane, and a ship) or a monitoring camera.

What is claimed is:

1. An imaging device comprising:
    an image sensor that has an imaging surface on which a plurality of pixels are two-dimensionally arranged and that generates image data from a subject image formed on the imaging surface; and an optical system that forms the subject image in a predetermined range of a vertical view angle and in a predetermined range of a horizontal view angle on the imaging surface, wherein
for (1) a higher resolution image generated by the image sensor for a view angle having a particular size and (2) a lower resolution image generated by the image sensor for a view angle having the same particular size, a number of pixels used for capturing the higher resolution image is larger than a number of pixels used for capturing the lower resolution image,
the imaging surface includes a first region and a second region different from the first region,
the optical system forms the subject image on the imaging surface so as to cause resolution of a first subject image of the subject image in the first region to be higher than resolution of a second subject image of the subject image in the second region,
the imaging surface includes a third region different from the first region and the second region,
the optical system forms the subject image on the imaging surface so as to cause resolution of a third subject image of the subject image in the third region to be higher than the resolution of the second subject image, and
at least part of a region between the first region and the third region is formed by the second region.

2. The imaging device according to claim 1, wherein the optical system includes a free-form lens.

3. The imaging device according to claim 1, wherein the third region being a region separated from the first region.

4. The imaging device according to claim 1, wherein the image sensor captures the subject image inside a movable body.

5. The imaging device according to claim 4, wherein the movable body is one of an automobile, a railway vehicle, a ship, an airplane, an agricultural machine, and a constructional machine.

6. The imaging device according to claim 4, wherein
the movable body includes a seat with a headrest, and
the first region is arranged in a region where an image of the headrest is formed when the person does not sit in the seat.

7. The imaging device according to claim 1, wherein the image sensor receives light in a visible light region and light in an invisible light region.

8. An imaging system comprising:
the imaging device according to claim 1; and
a control device that analyzes the image data generated by the imaging device,
wherein the control device analyzes an image formed in the first region in an image indicated by the image data.

9. The imaging system according to claim 8, wherein
the image sensor receives light in a visible light region and light in an invisible light region, and
the control device performs analysis using the image data generated by receiving the light in the invisible light region.

10. The imaging system according to claim 8, wherein
the image data generated in the first region includes image data of an eye of the person and
the control device analyzes a change in the image data of the eye of the person.

* * * * *